US008879874B2

(12) United States Patent
Vey

(10) Patent No.: US 8,879,874 B2
(45) Date of Patent: Nov. 4, 2014

(54) INTRUDER DETECTION SYSTEM

(75) Inventor: Dean Vey, Fyshwick (AU)

(73) Assignee: Perimeter Security Industries Pty Ltd, Aranda, Australian Capital Territory (AU)

(*) Notice: Subject to any disclaimer, the term of this patent is extended or adjusted under 35 U.S.C. 154(b) by 616 days.

(21) Appl. No.: 13/132,683

(22) PCT Filed: Dec. 21, 2009

(86) PCT No.: PCT/AU2009/001675
§ 371 (c)(1),
(2), (4) Date: Jun. 3, 2011

(87) PCT Pub. No.: WO2010/071926
PCT Pub. Date: Jul. 1, 2010

(65) Prior Publication Data

US 2011/0249934 A1 Oct. 13, 2011

(30) Foreign Application Priority Data

Dec. 22, 2008 (AU) ................................ 2008906583

(51) Int. Cl.
*G02B 6/00* (2006.01)
*A61M 11/08* (2006.01)
*G08B 13/186* (2006.01)
*G08B 13/12* (2006.01)

(52) U.S. Cl.
CPC ............ *G08B 13/186* (2013.01); *G08B 13/122* (2013.01)
USPC ........................................ 385/13; 128/200.23

(58) Field of Classification Search
None
See application file for complete search history.

(56) References Cited

U.S. PATENT DOCUMENTS

| | | | | |
|---|---|---|---|---|
| 5,134,386 | A | 7/1992 | Swanic | |
| 5,831,391 | A | 11/1998 | MacKay | |
| 7,532,781 | B2 | 5/2009 | Thompson et al. | |
| 2006/0257066 | A1 | 11/2006 | Hill et al. | |
| 2008/0017193 | A1 * | 1/2008 | Jones et al. | 128/200.23 |

FOREIGN PATENT DOCUMENTS

| | | | |
|---|---|---|---|
| DE | 19653250 | A1 | 6/1998 |
| GB | 2 406 376 | A1 | 3/2005 |
| WO | 94/18649 | A1 | 8/1994 |
| WO | 02/073561 | A1 | 9/2002 |
| WO | 2008/011058 | A2 | 1/2008 |

OTHER PUBLICATIONS

Supplementary European Search Report dated Apr. 24, 2012 corresponding to EP 09 83 3926.

* cited by examiner

*Primary Examiner* — Tina Wong
(74) *Attorney, Agent, or Firm* — Davis & Bujold, PLLC

(57) ABSTRACT

An intruder detection system including a light emitting unit, a light guide, and a light receiving unit. The light emitting unit is arranged to emit light into the light guide and the light guide is arranged to guide the light to the light receiving unit. The impact of an intruder on the light guide causes changes in the characteristics of the light received at the light receiving unit.

4 Claims, 3 Drawing Sheets

INTRUDER DETECTION SYSTEM

This application is a National Stage completion of PCT/AU2009/001675 filed Dec. 21, 2009, which claims priority from Australian patent application serial no. 2008906583 filed Dec. 22, 2008.

TECHNICAL FIELD

The present invention relates to intruder detection systems and particularly relates to perimeter intruder detection systems.

BACKGROUND TO THE INVENTION

There is a need to maintain security of buildings, storage areas, and other facilities to guard against theft, vandalism and other types of damage. This security can be provided by way of a perimeter intruder detection system which is set to detect an intrusion, and to transmit some type of alarm signal.

Some have tried to use optical fibre based intrusion detection systems that operate on the principle of speckle analysis. A speckle pattern is a random intensity pattern produced by the mutual interference of a set of wavefronts. In one intrusion detection system based on this principle a length of optical fibre is attached along a perimeter fence. Laser light of known frequency is introduced at both ends of the optical fibre. Two-dimensional optodetectors are attached at each end of the optical fibre by way of optical splitters which detect the speckle pattern produced by interference of the laser light. The output of the optodetectors is monitored for changes in their speckle patterns.

If the fence is tampered with, then this causes disturbance of the optical fibre and changes in the speckle pattern. This indicates that the fence may be being tampered with and an alarm signal is generated.

The use of laser light and speckle analysis requires the use of laser light sources and sensitive optodetectors along with equipment to monitor the outputs for changes in the speckle pattern. These components can be complex and are thus costly to implement, configure and maintain. There remains a need for alternative intrusion detection systems.

SUMMARY OF THE INVENTION

In a first aspect the present invention provides an intruder detection system including: a light emitting means; a light guide; a light receiving means; the light emitting means is arranged to emit light into the light guide; the light guide is arranged to guide the light to the light receiving means; the impact of an intruder on the light guide causes changes in the characteristics of the light received at the light receiving means.

The light emitting means may include a light emitting diode.

The light receiving means may be arranged to measure the intensity of the received light.

The light receiving means may include a light dependent resistor.

The light guide may include at least one optical fibre.

At least one optical fibre may be convoluted.

At least one convoluted optical fibre may be embedded in a mat.

In a second aspect the present invention provides a method of detecting intrusion into an area including the steps of: providing a system according to the first aspect of the invention; and deploying the light guide by laying it on the ground around the perimeter of the area.

BRIEF DESCRIPTION OF THE DRAWINGS

Embodiments of the present invention will now be described, by way of example only, with reference to the accompanying drawings, in which.

DETAILED DESCRIPTION OF THE PREFERRED EMBODIMENT

Figure 1:
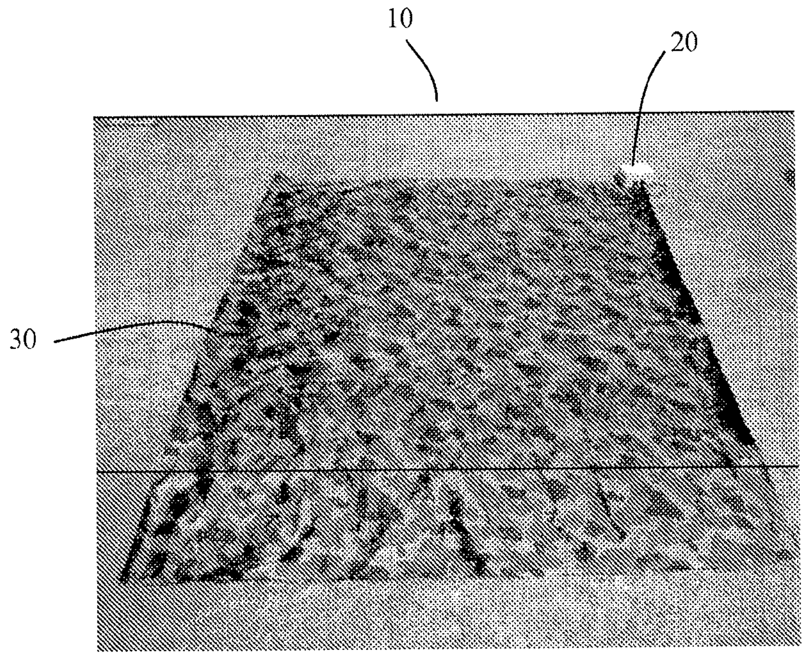
FIG. 1 depicts an intruder detection system according to an embodiment of the invention.

Referring to FIG. 1, a system for detecting intruders 10 is shown comprised of a light guide in the form of optical fibre embedded in mat 30 and a control box 20. The optical fibre is convoluted with such a density that it is difficult for a person to stand on the mat and not at the same time be standing on a portion of the embedded optical fibre.

Figure 2:
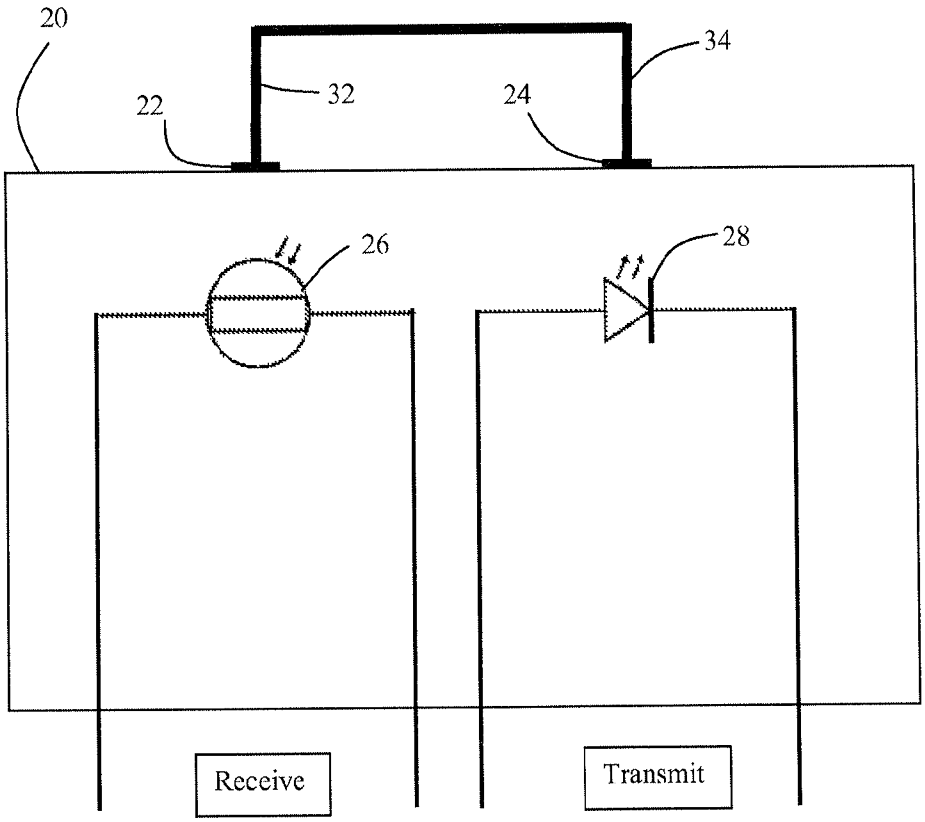
FIG. 2 is a schematic view of the control box of FIG. 1.

Referring to FIG. 2, the control box 20 is shown in schematic detail and includes a light emitting means in the form of light emitting diode (LED) 28 and a light receiving means in the form of light dependent resistor (LDR) 26. One end 32 of the optical fibre embedded in mat 30 is connected to junction 22 in light communication with light dependent resistor 26. The other end 34 of the optic fibre is connected to junction 24 in light communication with light emitting diode 28. In the figure, the optical fibre is depicted as being much shorter than it is in reality for ease of illustration. The portion of the optical fibre between ends 32, 34 is in fact of considerable length and is embedded in a mat. The fibre may be of the order of 100 m to 1000 m in length.

When power is applied to light emitting diode 28 it emits light which enters the optical fibre end 34. The light is guided through the convoluted optical fibre in mat 30 to exit the optical fibre end 32 and be received by light dependent resistor 26. The resistance of light dependent resistor 26 varies depending upon the intensity of light received.

The passage of light through the optical fibre is affected by disturbances to the optical fibre. Thus, when a person stands on the mat, and disturbs the optical fibre, this is reflected in a change of the intensity of light received at light dependent resistor 26 with a consequential change to the resistance of the light dependent resistor 26. Thus, changes in resistance of light dependent resistor 26 are indicative of disturbance of the optical fibre in the mat.

If the changes in resistance of light dependent resistor deviate from steady state conditions by a pre-determined threshold, then this indicates that the mat is being disturbed and an alarm is given to a potential intrusion.

Figure 3:
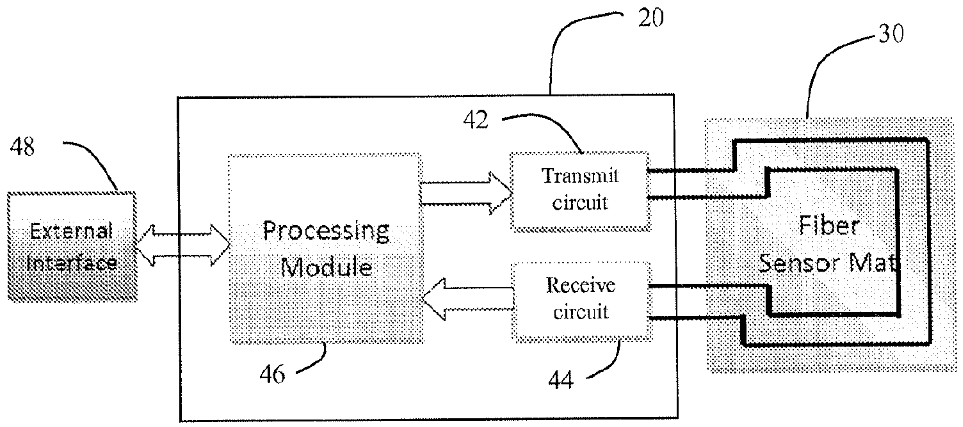
FIG. 3 is a schematic view of the control box and mat of FIG. 1.

Referring now to FIG. 3, the operation of the system is explained in further detail. The hardware for the control box consists of the following main components: processing module 46, transmit circuit 42, receive circuit 44, external-interface 48.

The external interface 48 is designed for flexibility and can be coupled to the following optional modules to provide real-time information such as alarms and system status: RS-232 cable connection for PC-based systems, RS-485 cable network for multiple mat applications, GSM/GPRS module with SMS and data capability for remote applications The processing module 46 consists of a microcontroller such as a Texas Instruments MSP430F2274 microcontroller. The microcontroller is a high-performance, low-cost, and low-power microprocessor which incorporates many peripherals into a single integrated circuit. This provides a versatile platform for the operation of the system. The processing module is responsible for controlling the transmit circuit and generating and analysing information from the receive circuit. In addition, the module also incorporates a serial link which provides a means for two-way data communication to the outside world.

The transmit circuit 42 consists of four Light Emitting Diodes (LED) driven by the processor via a specially designed Pulse-Width Modulated (PWM) circuit. The width of the pulse in the PWM signal as determined by software settings in the processor directly determines the amount of light output by the LED. The transmit circuit 42 also incorporates a circuit to monitor the bias current through the LED and hence, the light output. For each LED in the system, the drive circuit consists of a low-pass filter stage followed by a voltage-to-current (V-I) converter which is connected to the LED. The analog output of the V-I converter is buffered and fed back to the processor to form the LED bias monitor. In other embodiments, up to sixteen LEDs may be used.

The receive circuit 44 consists of at least one Light Dependent Resistor (LDR) corresponding to one for each LED in the system coupled to an analog front-end. Each front-end circuit in the system consists of a bias resistor for the LDR coupled to a band-pass filter stage whose output is buffered before being connected to the processor. The analog output produced from this circuit is directly proportional to the disturbance in the mat and it is this signal that the processor module continually analyses to determine alarm conditions.

The external interface 48 utilises the inbuilt communication interface within the processor module. This is a standard Universal Asynchronous Receive Transmit (UART) device which provides a byte-oriented (8-bit) serial interface. The actual hardware that forms the external interface is dependent on the actual interface that is required for the system.

The main function of the system is to monitor the mat and determine if an alarm condition is present or not. To accomplish this, the processor uses the inbuilt analog-to-digital converter to sample the analog value directly off the LDR and convert it to a 10-bit digital number. These numbers are then used in the sample and alarm processing routines as described in the next section. In addition to this, the processor also drives and monitors the LED bias current, monitors ambient temperature of the electronics, and continually provides an on demand communications channel.

The receive signal from the LDR is ac-coupled as well as low-pass filtered with a corner frequency of approximately 20 Hz. This allows a band-pass response which rejects electronic noise as well as low frequency drift from temperature and power supply variations while still allowing detection of footsteps. The processor continuously samples the LDR output at 50 Hz and analyses each sample as it appears. A continuous standard deviation (SD) of the raw signal is calculated to provide information on noise and steady state conditions within the system. This SD is then used to provide a moving trigger window around the signal which allows the system to adapt to varying operational conditions as necessary. The system is "pre-triggered" when the first negative-going sample is detected outside this window. If the next sample is also outside this window, the system goes into a data collection phase where it analyses and gathers information about the following 64 samples (1.28 s) in real-time. At the end of the collection phase, the system applies a signature analysis routine to the information to determine the nature of the event. The outcome of the routine is to classify the event and trigger an alarm if the required parameters are met. The parameters may be determined by trial and error.

The system is intended for deployment about the perimeter of a property such as a building site, commercial building, private dwelling, vacant land, airfield or any other property requiring protection of its perimeter against intruders. To deploy the system a number of mats are laid end to end along the edge of a perimeter. If there is a fence around the perimeter the mats are laid a small distance inside the fence. Each of the mats is connected to a control box. Each of the mats may be approximately 50 meters in length.

Power to the control boxes is provided by batteries or connection to main power. The control box may include, or be connected to, a GSM modem which can transmit a signal to a predetermined location in the event of an alarm or other condition such as low battery. An unlimited number of control boxes can be connected together to form a network and only one GSM modem is needed to interface to all of them. Each box has its own unique identity and becomes a separate zone within the system.

The mats used with the system may be made in a high visibility form such as using luminous colours or providing prominent warning notices. In this form the system provides overt surveillance, rather than covert surveillance. The principle of overt surveillance is that opportunistic intruders are deterred by being made aware that there is a security system in place.

It can be seen that embodiments of the invention have at least the following advantages:

Use of low cost components such as LDR and LED provides an affordable and robust intruder detection solution.

The system is versatile and can be easily deployed and uninstalled.

Any reference to prior art contained herein is not to be taken as an admission that the information is common general knowledge, unless otherwise indicated.

Finally, it is to be appreciated that various alterations or additions may be made to the parts previously described without departing from the spirit or ambit of the present invention.

The invention that may be claimed include the following arrangements, either singularly or in any combination thereof:

1. An intruder detection system comprising:

a light emitter;

a light guide;

a light receiver;

the light emitter being arranged to emit light into the light guide;

the light guide being arranged to guide the light to the light receiver;

the light guide being flexible such that an impact of an intruder on the light guide flexes the light guide and causes changes in characteristics of the light received at the light receiver; the light receiver being arranged to measure intensity of the received light; and the light receiver including a light dependent resistor; and the light emitter including a light emitting diode.

2. The intruder detection system according to claim 1, wherein the light guide comprises at least one optic fiber.

3. The intruder detection system according to claim 2, wherein the at least one optic fiber is convoluted.

4. The intruder detection system according to claim 3, wherein the at least one convoluted optic fiber is embedded in a mat.

* * * * *